(12) United States Patent
Popp et al.

(10) Patent No.: US 8,221,378 B2
(45) Date of Patent: Jul. 17, 2012

(54) COMBINATION OF REFASTENABLE AND RELEASABLE BONDS

(75) Inventors: Robert L. Popp, Hortonville, WI (US); Walter A. Mattingly, Appleton, WI (US); Thomas E. Williamson, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1151 days.

(21) Appl. No.: 11/215,865

(22) Filed: Aug. 30, 2005

(65) Prior Publication Data
US 2007/0049890 A1  Mar. 1, 2007

(51) Int. Cl.
*A61F 13/15* (2006.01)
(52) U.S. Cl. .................. 604/387; 604/385.03
(58) Field of Classification Search ............ 604/385.01, 604/385.03, 386–390
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 4,340,563 A | 7/1982 | Appel et al. |
| 4,663,220 A | 5/1987 | Wisneski et al. |
| 4,704,116 A | 11/1987 | Enloe |
| 4,720,415 A | 1/1988 | Vander Wielen et al. |
| 4,940,464 A | 7/1990 | Van Gompel et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,607,537 A | 3/1997 | Johnson et al. |
| 5,622,589 A | 4/1997 | Johnson et al. |
| 5,624,429 A * | 4/1997 | Long et al. ............... 604/391 |
| 5,662,638 A | 9/1997 | Johnson et al. |
| 6,113,717 A | 9/2000 | Vogt et al. |
| 6,409,858 B1 | 6/2002 | Popp et al. |
| 6,454,752 B1 | 9/2002 | Huang et al. |
| 6,514,187 B2 | 2/2003 | Coenen et al. |

(Continued)

FOREIGN PATENT DOCUMENTS

EP  1 523 968 A1  4/2005

(Continued)

OTHER PUBLICATIONS

Patent Cooperation Treaty Search Report from the International Search Authority, International Application No. PCT/US 2006/030599 dated Jan. 19, 2007.

*Primary Examiner* — Michele M Kidwell
(74) *Attorney, Agent, or Firm* — David J. Arteman (57) ABSTRACT

A refastenable, pant-like garment, including a chassis including a first waist region and a second waist region, together defining a waist opening and first and second leg openings. The garment also includes a first refastenable seam joining a first distal portion of the first waist region to a first distal portion of the second waist region. The first refastenable seam includes a first refastenable bond connecting the first distal portion of the first waist region and the first distal portion of the second waist region having a first refastenable bond peel strength.

18 Claims, 6 Drawing Sheets

U.S. PATENT DOCUMENTS

| | | |
|---|---|---|
| 6,520,946 B1 | 2/2003 | Krueger |
| 6,572,601 B2 * | 6/2003 | Suprise et al. ................ 604/391 |
| 6,596,107 B2 | 7/2003 | Stopher |
| 6,723,034 B2 | 4/2004 | Durrance et al. |
| 6,764,475 B1 | 7/2004 | Olson |
| 2001/0034512 A1 | 10/2001 | Karlsson et al. |
| 2002/0123730 A1 | 9/2002 | Popp et al. |
| 2002/0138064 A1 | 9/2002 | Datta et al. |
| 2002/0165514 A1 * | 11/2002 | Datta et al. ................ 604/385.11 |
| 2002/0173767 A1 | 11/2002 | Popp et al. |
| 2003/0062113 A1 | 4/2003 | Van Eperen et al. |
| 2003/0111168 A1 | 6/2003 | Olson et al. |
| 2003/0221767 A1 | 12/2003 | Vogt et al. |
| 2003/0225390 A1 | 12/2003 | Vogt et al. |
| 2003/0226862 A1 | 12/2003 | Vogt et al. |
| 2004/0007318 A1 | 1/2004 | Popp et al. |

FOREIGN PATENT DOCUMENTS

| | | |
|---|---|---|
| WO | WO 95/29657 A1 | 11/1995 |
| WO | WO 02/11654 A2 | 2/2002 |
| WO | WO 02/11657 A2 | 2/2002 |
| WO | WO 02/26182 A2 | 4/2002 |
| WO | WO 02/076359 A2 | 10/2002 |
| WO | WO 03/057108 A1 | 7/2003 |

* cited by examiner

COMBINATION OF REFASTENABLE AND RELEASABLE BONDS

BACKGROUND

Pant-like absorbent garments, such as adult incontinence wear, infant and children's diapers, swim wear and training pants, typically have adhesive or mechanical fasteners on the sides for donning and removal, or else rely on a stretchable waist opening and leg openings to slide on and off the wearer. Absorbent garments that slide on and off a wearer can be messy after use. Furthermore, in order to remove such absorbent garments, the wearer's clothing covering the absorbent garments, such as pants, must generally be completely removed. Checking the status of the wearer's absorbent garment contents can be just as cumbersome as changing the absorbent garment.

Refastenable seams including mechanical fasteners, such as, for example, hook and loop fasteners, have been found to be particularly beneficial when used in conjunction with pant-like absorbent garments. Refastenable seams allow for the garment to be easily applied and removed, as well as periodically opened to check for exudates and closed if no exudates are found.

Refastenable seams generally perform much better in shear than in peel. However in the manufacturing process butt seam are generally less complicated to construct than lap seams. Butt seams are stressed predominantly in peel, while lap seams are stressed predominantly in shear. As a result, there is a need or desire for refastenable seam that can be constructed as a butt seam but will convert to a lap seam.

SUMMARY

In response to the foregoing need, the present inventor undertook intensive research and development efforts that resulted in the discovery of a combination of refastenable and releasable bond. One version of the present invention includes a prefastened article, including a chassis including a first waist region and a second waist region, together defining a waist opening and first and second leg openings. The article also includes a refastenable seam joining a first distal portion of the first waist region to a first distal portion of the second waist region. The refastenable seam includes a first refastenable bond connecting the first distal portion of the first waist region and the first distal portion of the second waist region having a first refastenable bond peel strength. The first distal portion of the first waist region is folded and bonded with a releasable bond having a first releasable bond peel strength. Further the first refastenable bond peel strength is greater than the first releasable bond peel strength.

Another version of the present invention provides a refastenable, pant-like garment, including a chassis including a first waist region and a second waist region, together defining a waist opening and first and second leg openings. The garment also includes a first refastenable seam joining a first distal portion of the first waist region to a first distal portion of the second waist region. The first refastenable seam includes a first refastenable bond connecting the first distal portion of the first waist region and the first distal portion of the second waist region having a first refastenable bond peel strength. The first distal portion of the first waist region being folded and bonded with a releasable bond having a first releasable bond peel strength. Further the first refastenable bond peel strength is greater than the first releasable bond peel strength. The garment also includes a second refastenable seam joining a second distal portion of the first waist region to a second distal portion of the second waist region. The second refastenable seam includes a second refastenable bond connecting the second distal portion of the first waist region and the second distal portion of the second waist region having a second refastenable bond peel strength. The second distal portion of the first waist region being folded and bonded with a releasable bond having a second releasable bond peel strength. Further the second refastenable bond peel strength is greater than the second releasable bond peel strength. Still another version of the present invention includes a refastenable joint joining a first material having a first end and a second end to a second material having a third end and a fourth end. The refastenable joint including a refastenable bond connecting the first end to the third end. The first material is folded and bonded with a releasable bond. Further separating the second end from the fourth end initially stresses the refastenable bond and the releasable bond predominantly in peel, then ruptures the releasable bond predominantly in peel, then stresses the refastenable bond predominantly in shear.

DEFINITIONS

Within the context of this specification, each term or phrase below will include the following meaning or meanings.

"Attached" refers to the joining, adhering, connecting, bonding, or the like, of at least two elements. Two elements will be considered to be attached to one another when they are attached directly to one another or indirectly to one another, such as when each is directly connected to intermediate elements.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
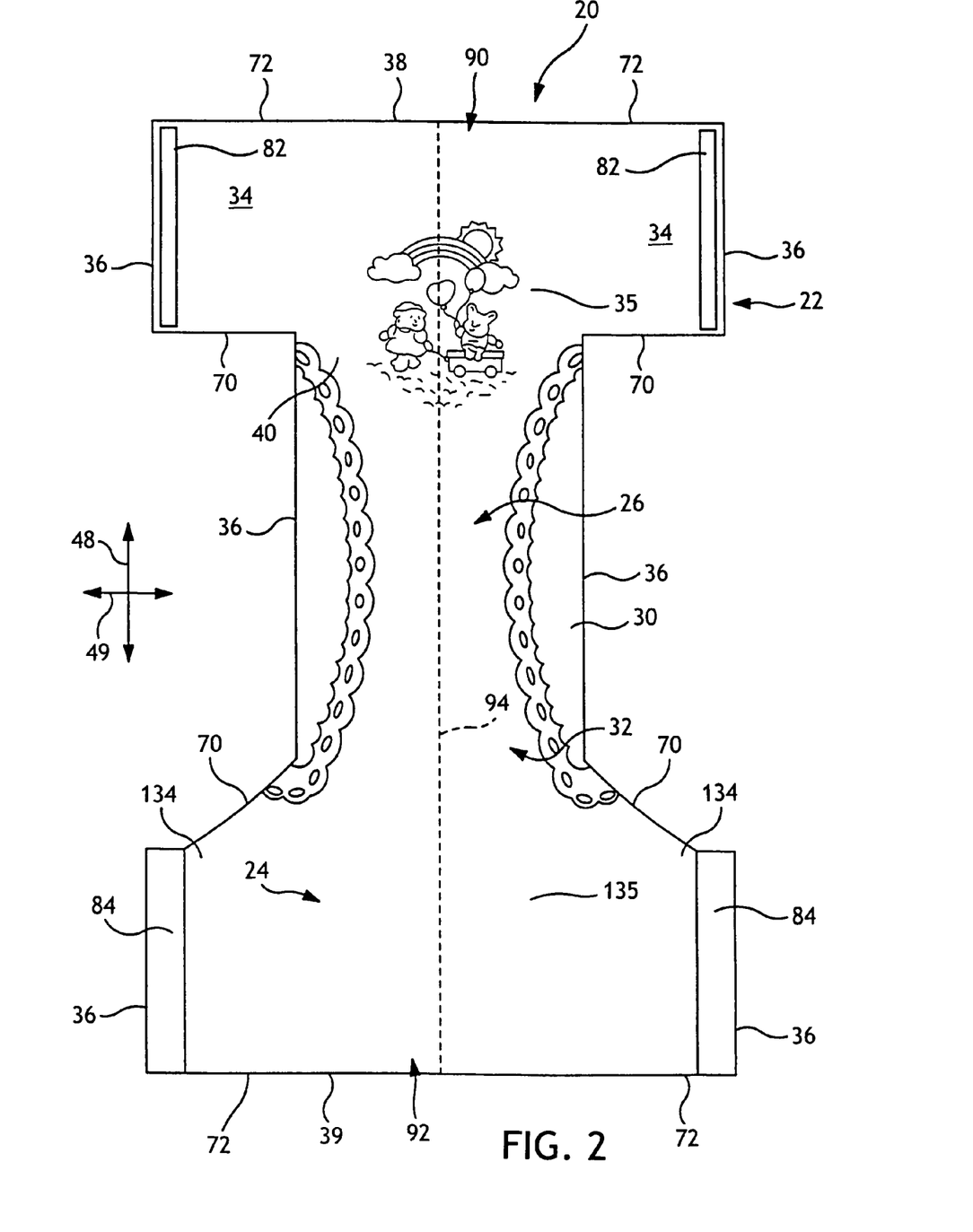
FIG. 2 is a plan view of an absorbent garment in a stretched flat state showing the surface of the garment that faces away from the wearer when the garment is worn.
Figure 3:
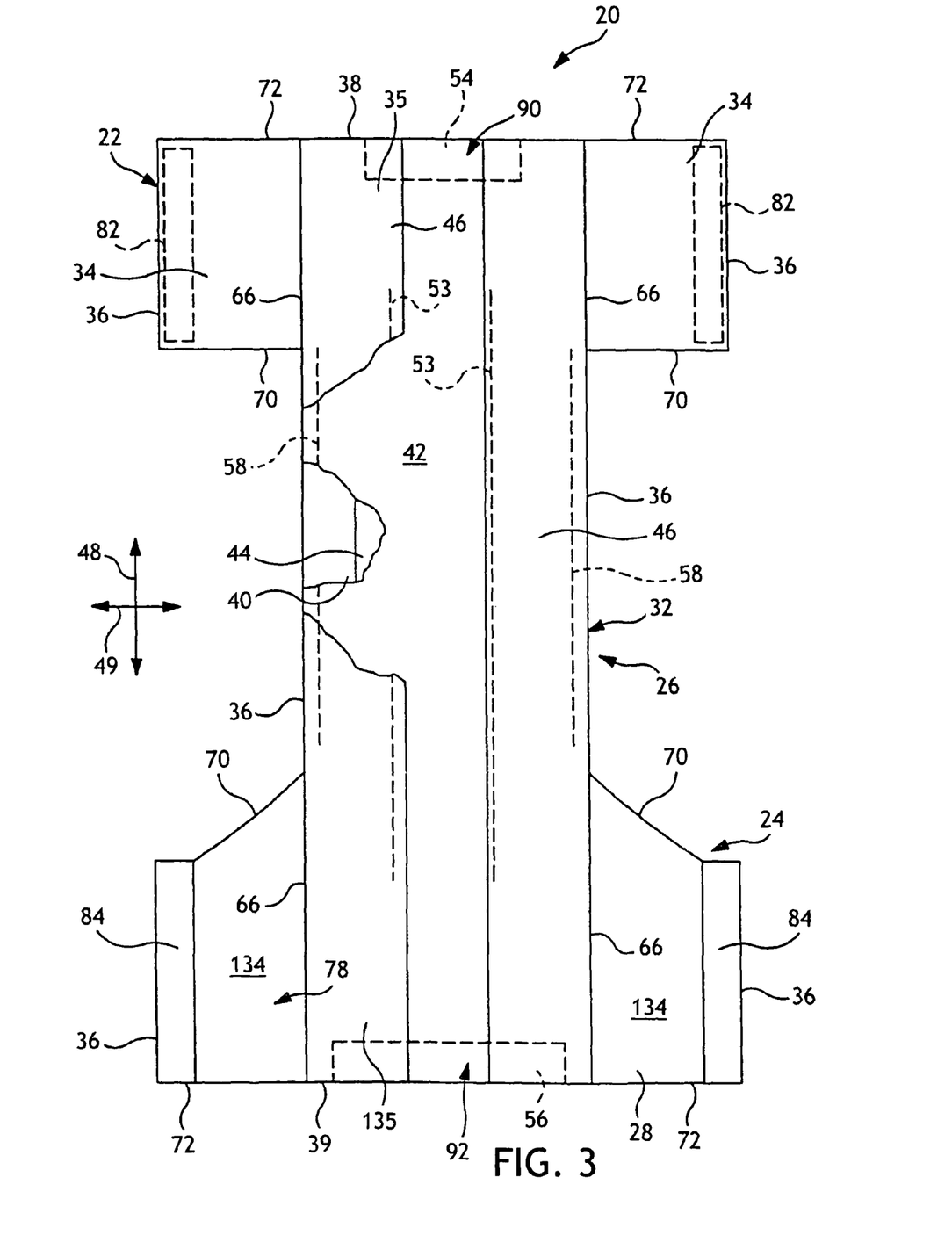
FIG. 3 is a plan view of an absorbent garment in a stretched flat state showing the surface of the garment that faces the wearer when the garment is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is generally longer in the longitudinal direction than in the transverse direction, although products longer in the transverse direction are also possible.

"Longitudinal midline" refers to a line, either real or imaginary, that runs along the longitudinal length of the chassis of an absorbent garment and bisects the chassis into two halves of equal transverse width.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Offset tucked" refers to a folded position of a garment wherein the front and back regions of the garment are skewed such that the longitudinal midline of the front region of the chassis is offset or not aligned with the longitudinal midline of the back region of the chassis, and seams connecting the front and back regions are tucked.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently attached" or "permanently bonded" refers to the joining, adhering, connecting, attaching, bonding, or the like, of two elements of an absorbent garment such that the elements tend to be and remain attached during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture. The refastenable elements can be attached, separated and reattached for at least one cycle, suitably for at least 5 cycles, or suitably for at least 10 cycles.

"A Releasable bond" and variations thereof refer to two elements being connected or connectable such that the elements tend to remain connected absent a separation force applied to one or both of the elements. The required separation force is typically less than that encountered while wearing the absorbent garment.

"Self-engaging fastener" refers to a fastening component that can engage with another fastening component having the same structure.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802, 817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 250% of its initial length, desirably to at least 300% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a nonsoftened condition when cooled to room temperature.

These terms may be defined with additional language in the remaining portions of the specification.

DETAILED DESCRIPTION OF THE PRESENTLY PREFERRED EMBODIMENTS

The present invention is directed to refastenable seams on garments. The principles of the present invention can be incorporated into any suitable disposable absorbent article having a pre-fastened and refastenable seam. Examples of such suitable articles include diapers, training pants, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Figure 1:
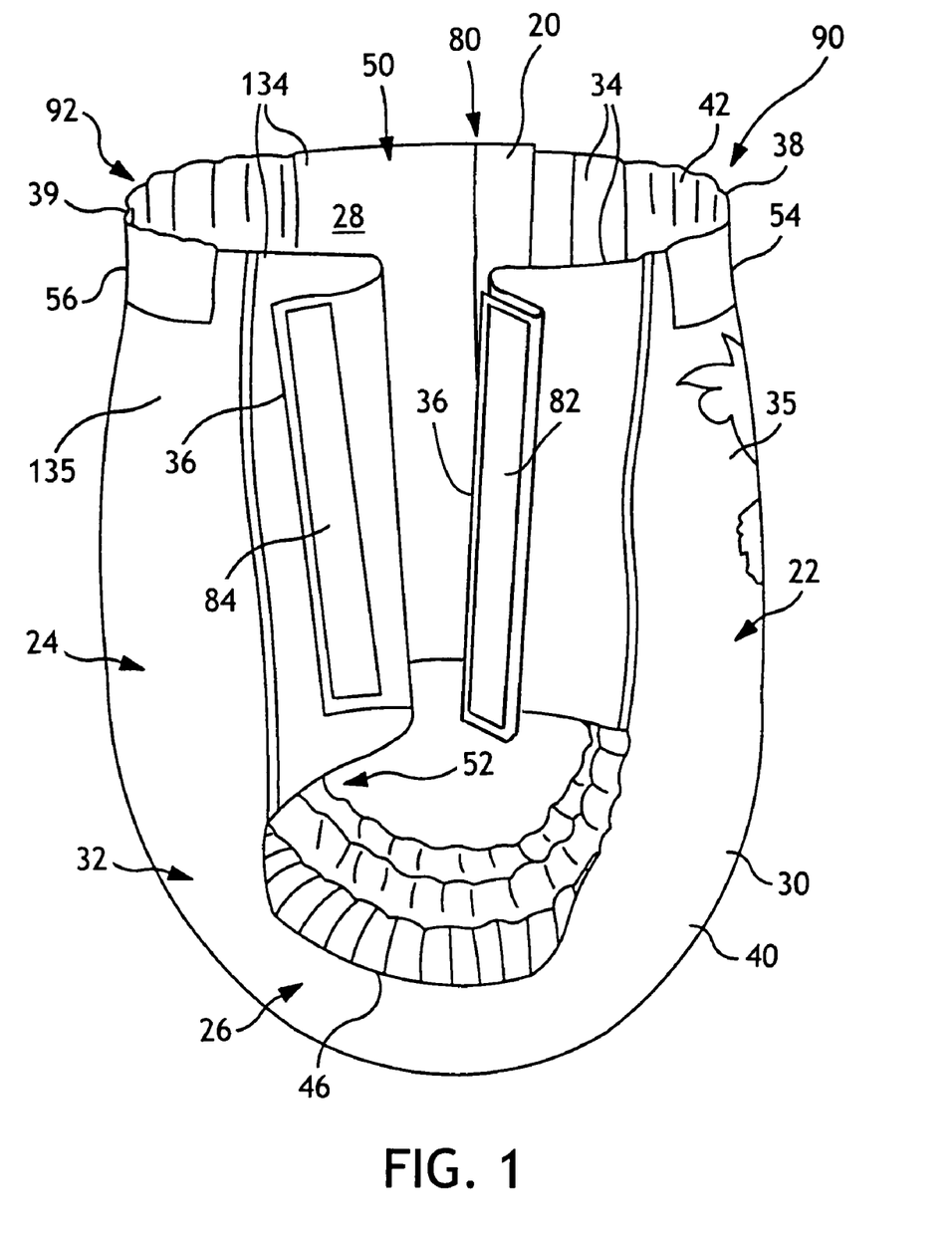
FIG. 1 is a perspective view of an absorbent garment having refastenable side seams.

Referring to FIG. 1, the training pant 20 includes an absorbent chassis 32 defining a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed distal edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a pair of transversely opposed front side panels 34 and a pair of transversely opposed back side panels 134. The front and back side panels 34, 134 are formed along the distal edges 36 of the chassis and can either be integrally formed with the chassis, as shown in FIG. 2, or can each include at least one separate element permanently attached to the chassis, as shown in FIGS. 1 and 3. For reference, arrows 48 and 49 depicting the orientation of the longitudinal axis and the transverse axis, respectively, of the training pant 20 are illustrated in FIGS. 2 and 3.

The illustrated absorbent chassis 32 can include an outer cover 40, a bodyside liner 42 which is connected to the outer cover in a superposed relation, an absorbent assembly 44 which is located between the outer cover 40 and the bodyside liner 42, and a pair of containment flaps 46, as shown in FIG. 3.

With the training pant 20 in the fastened position, as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34, 134 include the portions of the training pant 20 which, when worn, are positioned on the hips of the wearer.

As shown in FIG. 3, the front region 22 of the absorbent chassis 32 includes the transversely opposed front side panels 34 and a front panel 35 positioned between and interconnecting the side panels, along with a front waist elastic member 54 and any other connected components. A front waist region 90 is a region of the front panel 35 along the front waist edge 38. The back region 24 of the absorbent chassis 32 includes the transversely opposed back side panels 134 and a back panel 135 positioned between and interconnecting the side panels, as well as a rear waist elastic member 56 and any other connected components. A back waist region 92 is a region of the back panel 135 along the back waist edge 39. The waist edges 38 and 39 of the absorbent chassis 32 are configured to encircle the waist of the wearer when worn and provide the waist opening 50 which defines a waist perimeter dimension. Portions of the transversely opposed distal edges 36 of the chassis 32 in the crotch region 26, along with leg end edges 70 of the side panels 34 and 134, generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed distal edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39 as well as over waist edges 72 of the side panels 34, 134, and can extend over part or all of the waist edges. The leg elastic members 58 can be operatively joined to the outer cover 40 and/or bodyside liner 42 while longitudinally aligned along the distal edges 36 and positioned in the crotch region 26 of the chassis 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. As mentioned, the bodyside liner 42 and/or the outer cover 40 can be made of a fastening component material or a mating fastening component material to eliminate the need for separately attached mating fastening components.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema, Inc., a division of ICI of New Castle, Del., and GLUCOPON® 220UP from Cognis Corp. of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. High absorbency material can be provided in any form known in the art, including but not limited to particles, fibers, foams and films.

In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34, 134 disposed on each side of the absorbent chassis 32. These transversely opposed front side panels 34 and transversely opposed back side panels 134 can be permanently bonded to the front panel 35 and back panel 135 in the respective front and back regions 22, 24 along attachment lines 66, and are attached to one another. The side panels 34, 134 may be permanently attached using attachment means known to those skilled in the art such as adhesive, thermal or ultrasonic bonding. As mentioned, the side panels 34, 134 can also be formed as continuous extensions of the front and back panels 35, 135.

As shown in FIG. 1, the fastening component 82 can be permanently bonded to either the inner surface 28 or the outer surface 30 of each front side panel 34 adjacent each distal edge 36 of the front region 22 of the chassis 32, and the mating fastening components 84 can be permanently bonded to either the inner surface 28 or the outer surface 30 of each back side panel 134 adjacent each distal edge 36 of the back region 24 of the chassis, or either the inner surface 28 or the outer surface 30 of the chassis 32 can include fastening material 86 or mating fastening material 88. The fastening components 82 and the mating fastening components 84 may be attached to the side panels 34 and the chassis 32 using attachment means known to those skilled in the art such as adhesive, thermal or ultrasonic bonding.

The fastening component may comprise adhesive, cohesive, tape, hook and loop, or any other refastenable attachment means know in the art. In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. In yet another embodiment, half of the fastening components 82 and half of the mating fastening components 84 can include hook type fasteners, while half of the fastening components 82 and half of the mating fastening components 84 can include loop type fasteners. In still another embodiment, each of the fastening components 82 and the mating fastening components 84 include self-engaging fasteners. The fastening components 82 and the mating fastening components 84 are desirably rectangular, although they may alternatively be square, round, oval, curved, discontinuous such as multiple fasteners, or any other suitable shape. The fastening components 82 and mating fastening components 84 may or may not be parallel to a longitudinal midline 94 of the garment 20.

In another embodiment, the nonwoven web in the outer cover 40 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In yet another embodiment, the nonwoven web in the bodyside liner 42 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In still another embodiment, an inner or outer surface of either the front side panels 34 or the back side panels 134 can include a loop-type fastening material, thereby eliminating the need for separate loop type fastening components 82 or 84.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. Suitable hook material can be molded or extruded of nylon, polypropylene or another suitable material. Suitable single-sided hook materials for the fastening components 82 or the mating fastening components 84 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In particular embodiments for improved fit and appearance, the side panels 34, 134 desirably have an average length dimension measured parallel to the longitudinal axis 48 that is about 15 percent or greater, and particularly about 25 percent or greater, of the overall length dimension of the absorbent article, also measured parallel to the longitudinal axis 48. For example, in training pants having an overall length dimension of about 54 centimeters, the side panels 34, 134 desirably have an average length dimension of about 10 centimeters or greater, such as about 15 centimeters. A waist end edge 72 of each side panel 34, 134 can suitably be relatively straight across in the transverse direction while the leg end edge 70 of each side panel 34, 134 can suitably have a curvature, as shown in FIGS. 2 and 3, to allow the leg opening 52 to conform about a wearer's leg.

Each of the side panels 34, 134 can include one or more individual, distinct pieces of material in addition to the fastening components 82, 84, as shown in FIG. 3. In particular embodiments, for example, each side panel 34, 134 can include first and second side panel portions that are joined at a seam, with at least one of the portions including an elastomeric material. The side panels 34, 134 desirably include an elastic material capable of stretching in a direction generally parallel to the transverse axis 49 of the training pant 20. The front side panels 34 and the back side panels 134 can be of equal widths or of different widths in the transverse direction.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and U.S. Pat. No. 4,720,415 issued Feb. 2, 1992 to Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

Figure 4:
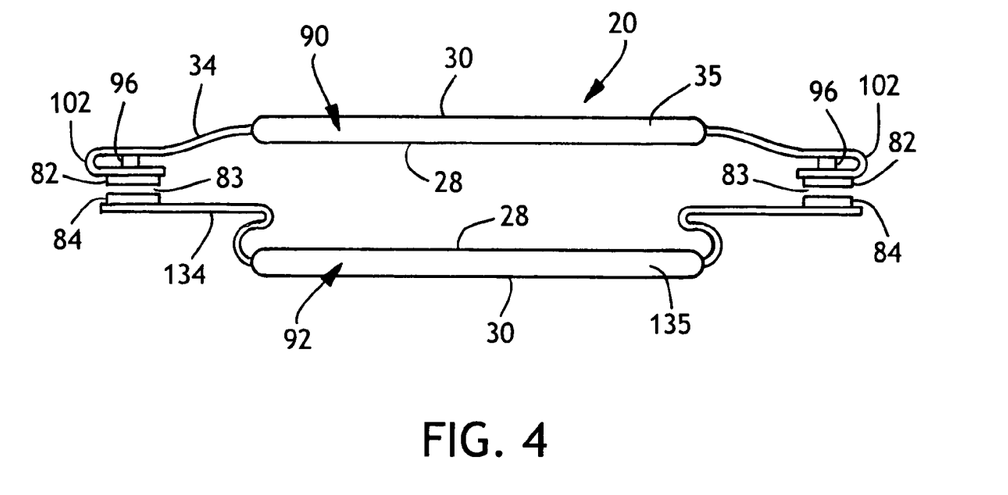
FIGS. 4 and 4A illustrate top views of a waist region of an absorbent garment illustrating a first version of refastenable seams of the present invention.

FIG. 4 illustrates a view of a training pant 20 including a refastenable bond 83 and a releasable bond 96 of the present invention. The training pant 20 includes a fastening component 82 disposed in a first waist region, specifically as shown attached to the front side panel 34. The training pant 20 also includes a mating fastening component 84 disposed in the second waist region, specifically as shown attached to the back side panel 134. The fastening components 82, 84 define a refastenable bond 83. The training pant 20 also includes a releasable bond 96, which bonds a portion of the front side panel 34 to a second portion of the front side panel 34 maintaining a fold 102 in the front side panel 34. The fold 102 and releasable bond 96 are positioned such that the fastening component 82, while disposed on the outer surface of the front panel 34, faces the inner surface 28 of the back side panel 134.

This arrangement of bonds 83, 96 and fold 102 may provide many benefits, first of which may be ease of manufacture. During manufacture, the training pant 20 may be constructed from a flat elongated web. The releasable front side panel 34 may be folded and releasably bonded 96. The fastening components 82, 84 may then be placed on the side panels 34, 134 (both applied from the inner surface 28 side of the elongated web). The elongate web may then be cut into discrete articles. To form the closed training pant 20, the discrete article is folded along the transverse axis 49 bringing the front side panel 34 and rear side panel 134 into face to face contact, forming a refastenable bond 83 with the fastening components 82, 84.

Figure 4A:
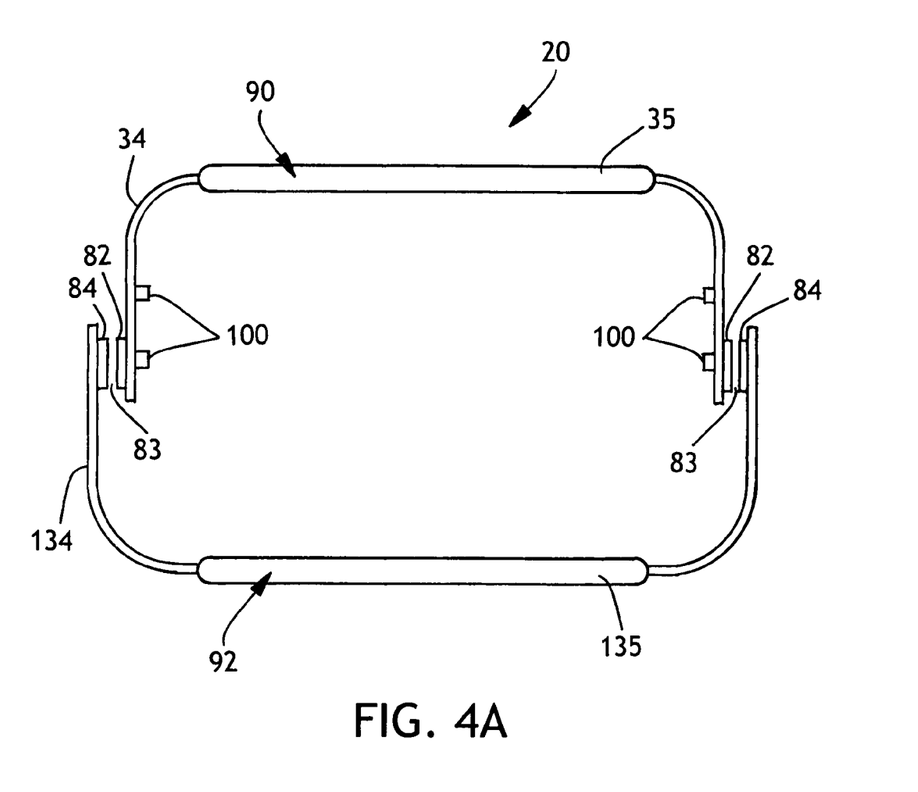

FIG. 4A illustrates a view of a training pant 20 including a refastenable bond 83 and a releasable bond 96 of the present invention after the front waist region 90 has been separated from the back waist region 92. As illustrated in FIG. 4, separating the front waist region 90 from the back waist region 92 initially stresses the refastenable bond 83 and the releasable bond 96 predominantly in peel. Further separation of the waist regions 92, 94 ruptures the releasable bond 96 predominantly in peel (releasable bond after rupture 100). Continued separation of the waist region 92, 94, stresses the refastenable bond 83 predominantly in shear. The arrangement of the releasable bond 96, refastenable bond 83 and fold 102, may provide great benefits in the manufacture, strength and aesthetics of refastenable bond 83.

One way to construct the combination of side panels 34, 134 is by utilizing bonds 82, 84, 96 with the appropriate relative peel strengths. The peel strength of the refastenable bond 83 may be chosen to be greater than the peel strength of the releasable bond 96. The ratio of the refastenable bond peel strength to the releasable bond peel strength may be greater than 1.5, alternatively greater than 5, alternatively greater than 10, alternatively greater than 25, alternatively greater than 50.

The releasable bond 96 may include ultrasonic bonding, pressure bonding, thermal bonding, adhesive bonding, cohesive bonding, magnetic bonding or any combination thereof. The releasable bond 96 may also include hook and loop. The releasable bond 96 may be chosen such the releasable bond after rupture 100 is skin friendly as contact with a wearer's skin is possible.

Peel Strength Test

This procedure is a tensile bench test to measure the peel force required to separate a mechanical fastening system that joins two materials. The peel force of separation is measured by determining load values as the two materials are pulled apart perpendicular to their plane of contact. The direction of removal (peel), in this application, is that direction in which the fastener material would generally be removed from a substrate when the product is in use. Peel strength is normalized by dividing by the contact area resulting in a force per area.

Equipment

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.

2. Software commercially obtained from MTS Sintech under the trade designation Sintech Testworks®.

3. Pnuematic-action grips commercially available from Instron Corporation, Canton, Mass., under the trade designation "Instron Model 2712-004."

4. 1 by 4 inch grip faces, serrated, commercially available from Instron Corporation, Canton, Mass.

5. Test facility having a temperature of 23±1° C., and a relative humidity of 50±2 percent.

Test Procedure

1. A sample to be tested is conditioned in the test facility for at least 4 hours prior to testing.

2. The load cell is calibrated and the software loaded.

3. The grips are installed on the tensile tester with the jaws closed.

4. The test condition for the tensile tester is set as follows:
Crosshead speed=500 millimeters/minute
Full-scale load=5 kilograms;
Threshold=5 percent;
Fail criterion=95 percent; and
Gage length=50 millimeters.

5. The weight of the clamp is tared out.

6. The ear portion on the back waist region of the article is inserted into the upper jaw such that the edge of the grip face is flush with the inner edge of the fastener material.

7. The front waist region of the article is inserted into the lower jaw such that the inner surface of the back waist region and the outer surface of the front waist region form a 180° angle. The lower jaw is closed.

8. The crosshead is started in motion.

9. The peak load of failure is recorded. It is intended that the mode of failure is that the back waist region of the diaper separates from the front waist region of the diaper.

Figure 5:
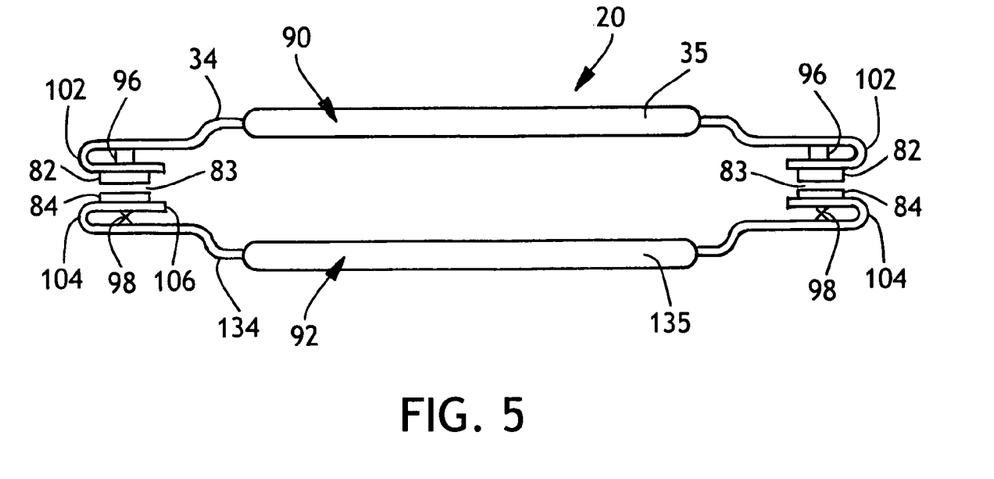
FIGS. 5 and 5A illustrate top views of a waist region of an absorbent garment illustrating a second version of refastenable seams of the present invention.

FIG. 5 illustrates a view of a training pant 20 including a refastenable bond 83, permanent bond 98 and a releasable bond 96 of the present invention. The training pant 20 includes a fastening component 82 attached to the chassis and disposed in a first waist region, specifically as shown attached to the front side panel 34. The training pant 20 also includes a mating fastening component 84 attached to the chassis and disposed in the second waist region, specifically as shown attached to the back side panel 134. The fastening components 82, 84 define a refastenable bond 83. The training pant 20 also includes a releasable bond 96, which bonds a portion of the front side panel 34 to a second portion of the front side panel 34 maintaining a fold 102 in the front side panel 34. The fold 100 and releasable bond 96 are positioned such that the fastening component 82, while disposed on the outer surface of the front panel 34, faces the inner surface 28 of the back side panel 134. The training pant 20 also includes a permanent bond 98, which bonds a portion of the back side panel 134 to a second portion of the back side panel 134 maintaining a fold 104 in the back side panel 134. The fold 104 and permanent bond 98 are positioned such that the fastening component 84, while disposed on the outer surface 30 of the back panel 134, faces the inner surface 28 of the front side panel 34.

The inclusion of the permanent bond 96 and fold 104 may provide additional benefits with regard to manufacture. The permanent bond 96 and fold 104 may be positioned such that width of the back side band 134 is reduced by the same amount as the width of the front side panel 34 is reduced by the releasable bond 96 and fold 102. If original width of the side panels 34, 134 is the same, this equal reduction may simplify the manufacturing process by aligning the fastening components 82, 84 when the training pant 20 is folded along the transverse axis 49 without further manipulation of the side panels 34, 134.

Figure 5A:
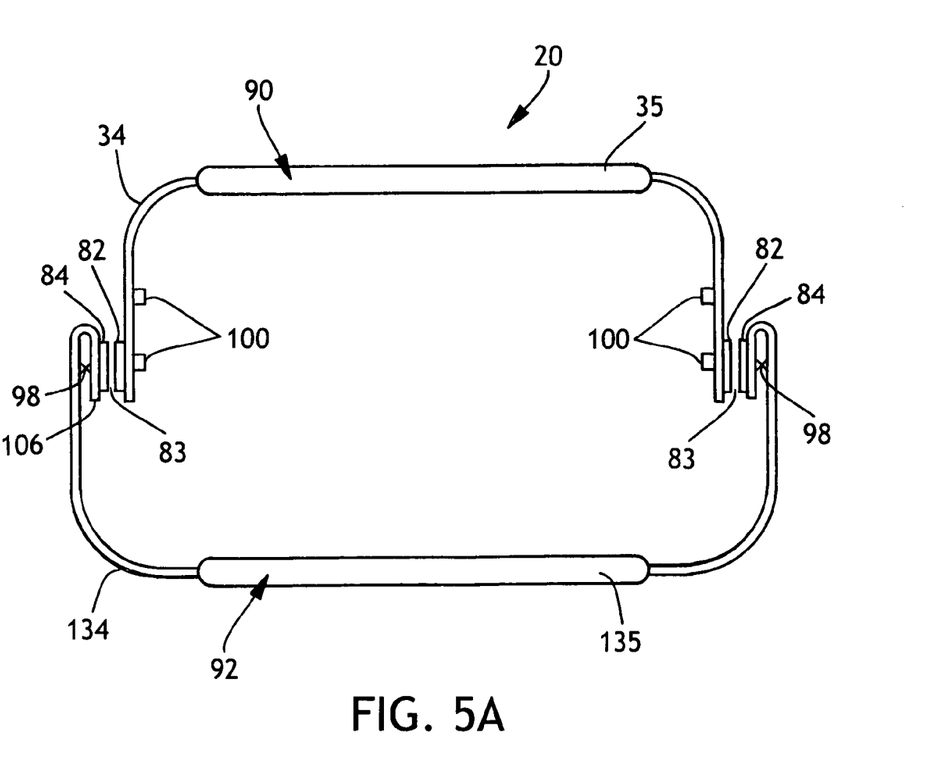

FIG. 5A illustrates a view of a training pant 20 including a refastenable bond 83, a permanent bond 98 and a releasable bond 96 of the present invention after the front waist region 90 has been separated from the back waist region 92. As illustrated in FIG. 5, separating the front waist region 90 from the back waist region 92 initially stresses the refastenable bond 83, the permanent bond 96 and the releasable bond 96 predominantly in peel. Further separation of the waist regions 92, 94 ruptures the releasable bond 96 predominantly in peel (releasable bond after rupture 100). Continued separation of the waist region 92, 94, stresses the refastenable bond 83, and permanent bond 96 predominantly in shear. The arrangement of the releasable bond 96, permanent bond 98, refastenable bond 83, and folds 102, 104, may provide great benefits in the manufacture, strength and aesthetics of releasable seam 80. The permanent bond 98 and fold 104 provides the added benefit in that the terminal end 106 of the back side panel 134 is not visible from the outside of the training pant 20, thereby presenting a more finished looking appearance.

The peel strength of the permanent bond 98 may be chosen to be greater than the peel strength of the releasable bond 96. The peel strength of the permanent bond 98 may be chosen to be greater than the peel strength of the refastenable bond 83. The ratio of the permanent bond peel strength to the releasable bond peel strength may be greater than 1.5, alternatively greater than 5, alternatively greater than 10, alternatively greater than 25, alternatively greater than 50.

The permanent bond 98 may include ultrasonic bonding, pressure bonding, thermal bonding, adhesive bonding, cohesive bonding, magnetic bonding or any combination thereof. The permanent bond 98 may also include hook and loop.

Figure 6A:
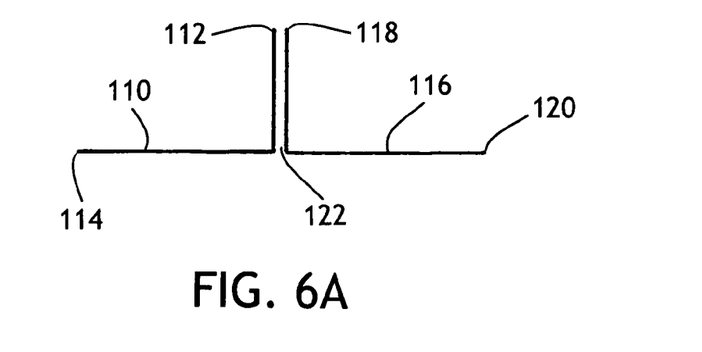
FIGS. 6A-6D illustrate several seams joining a first material to a second material 116.
Figure 6B:
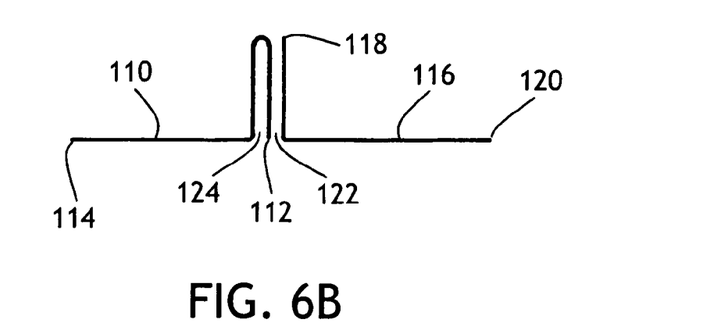

FIGS. 6A-D illustrate several seams joining a first material 110 having a first end 112 and a second end 114 and a second material 116 having a third end 118 and fourth end 120, specifically the first end 112 of the first material 110 to the third end 118 of the second material 116. FIGS. 6A and 6B illustrate butt seams. FIG. 6A illustrates a seam as previously known in the art. As used herein, the term "butt seam" refers to a seam or bond where the outer edges of the pieces of substrate project inward or outward from the finished product, as opposed to lying flat, thus placing the bond (122 in FIG. 6A, 122 and 124 in FIG. 6B) in peel, as opposed to shearing strain. FIG. 6B illustrates a combination of a refastenbable bond 122, and a releasable bond 124 which join a first end 112 of a first material 110 to a third end 118 of a second material 116. The first material 110 is folded and bonded with the releasable bond 124.

Separating the second end 114 of the first material 110 from the fourth end 120 of the second material 116 initially stresses the refastenable bond 122 and the releasable bond 124 predominantly in peel, then ruptures the releasable bond 124 predominantly in peel, then stresses the refastenable bond 122 predominantly in shear.

Figure 6C:
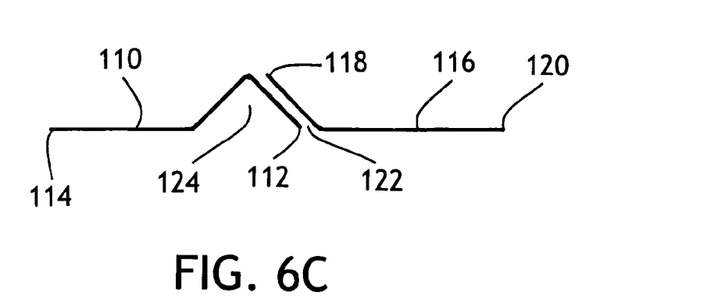
Figure 6D:
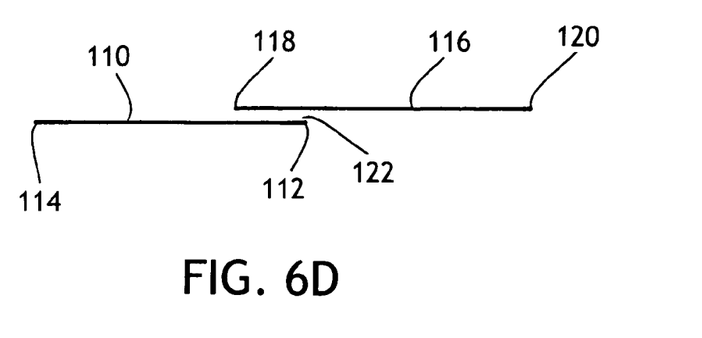

FIGS. 6B through 6D illustrate the conversion of a butt seam into a lap seam. The releasable bond 124 has a lower peel strength than refastenable bond 122; consequently, as force is applied to the combination of bonds 122, 124, releasable bond 124 will fail first. Upon failure of releasable bond 124, refastenable bond 124 is converted into a lap seam, thus placing the refastenable bond 124 in shear as opposed to peel strain.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A prefastened article, comprising:
a chassis including a first waist region and a second waist region, together defining a waist opening and first and second leg openings;
a refastenable seam joining a first distal portion of the first waist region to a first distal portion of the second waist region, and including a first refastenable bond connecting the first distal portion of the first waist region and the first distal portion of the second waist region having a first refastenable bond peel strength, the first distal portion of the first waist region being folded and bonded to itself with a releasable bond having a first releasable bond peel strength, wherein the first refastenable bond peel strength is greater than the first releasable bond peel strength.

2. The article of claim 1 wherein separating the first waist region from the second waist region initially stresses the refastenable bond and the releasable bond predominantly in peel, then ruptures the releasable bond predominantly in peel, then stresses the refastenable bond predominantly in shear.

3. The article of claim 2, wherein a ratio of the refastenable bond peel strength to the releasable bond peel strength is greater than 1.5.

4. The article of claim 2, wherein the ratio of the refastenable bond peel strength to the releasable bond peel strength is greater than 50.

5. The article of claim 1, wherein the refastenable bond comprises hook and loop, cohesive, adhesive or tape.

6. The article of claim 1, wherein the releasable bond comprises an ultrasonic bond.

7. The article of claim 1, wherein the releasable bond comprises a pressure bond.

8. The article of claim 1, wherein the releasable bond comprises an adhesive bond.

9. A process for providing a package of prefastened articles comprising:
manufacturing the article of claim 1;
rupturing the releasable bond; and
packaging the article.

10. A refastenable, pant-like garment, comprising:
a chassis including a first waist region and a second waist region, together defining a waist opening and first and second leg openings;
a first refastenable seam joining a first distal portion of the first waist region to a first distal portion of the second waist region, and including a first refastenable bond connecting the first distal portion of the first waist region and the first distal portion of the second waist region having a first refastenable bond peel strength, the first distal portion of the first waist region being folded and bonded to itself with a releasable bond having a first releasable bond peel strength, wherein the first refastenable bond peel strength is greater than the first releasable bond peel strength; and
a second refastenable seam joining a second distal portion of the first waist region to a second distal portion of the second waist region, and including a second refastenable bond connecting the second distal portion of the first waist region and the second distal portion of the second waist region having a second refastenable bond peel strength, the second distal portion of the first waist region being folded and bonded to itself with a releasable bond having a second releasable bond peel strength, wherein the second refastenable bond peel strength is greater than the second releasable bond peel strength.

11. The garment of claim 10, wherein the first distal portion of the second waist region is folded and bonded with a first permanent bond having a first permanent bond peel strength, the first permanent bond peel strength being greater than the first refastenable bond peel strength and the first releasable bond peel strength, and the second distal portion of the second waist region is folded and bonded with a first permanent bond having a second permanent bond peel strength, the second permanent bond peel strength being greater than the second refastenable bond peel strength and the second releasable bond peel strength.

12. The garment of claim 11, wherein the first and second permanent bonds comprise ultrasonic bonds.

13. The garment of claim 10, wherein a ratio of the first refastenable bond peel strength to the first releasable bond peel strength is greater than 1.5, and a ratio of the second refastenable bond peel strength to the second releasable bond peel strength is greater than 1.5.

14. The garment of claim 10, wherein a ratio of the first refastenable bond peel strength to the first releasable bond peel strength is greater than 50, and a ratio of the second refastenable bond peel strength to the second releasable bond peel strength is greater than 50.

15. The article of claim 10, wherein the first and second refastenable bonds comprise hook and loop, cohesive, adhesive or tape.

16. The article of claim 10, wherein the first and second releasable bonds comprise ultrasonic bonds.

17. The article of claim 10, wherein the first and second releasable bonds comprise pressure bonds.

18. The article of claim 10, wherein the first and second releasable bond comprise adhesive bonds.

* * * * *